United States Patent
Liu et al.

(10) Patent No.: US 12,196,762 B2
(45) Date of Patent: Jan. 14, 2025

(54) DEER-DERIVED SPECIFIC PEPTIDE AND DETECTION METHOD THEREFOR

(71) Applicant: NANJING UNIVERSITY OF CHINESE MEDICINE, Nanjing (CN)

(72) Inventors: Rui Liu, Nanjing (CN); Shuo Cai, Nanjing (CN); Mengtong Jiang, Nanjing (CN); Kexuan Zhao, Nanjing (CN); Jinao Duan, Nanjing (CN)

(73) Assignee: NANJING UNIVERSITY OF CHINESE MEDICINE, Nanjing (CN)

( * ) Notice: Subject to any disclaimer, the term of this patent is extended or adjusted under 35 U.S.C. 154(b) by 149 days.

(21) Appl. No.: 18/040,497

(22) PCT Filed: Nov. 26, 2020

(86) PCT No.: PCT/CN2020/131797
§ 371 (c)(1),
(2) Date: Feb. 3, 2023

(87) PCT Pub. No.: WO2022/048048
PCT Pub. Date: Mar. 10, 2022

(65) Prior Publication Data
US 2023/0266339 A1    Aug. 24, 2023

(30) Foreign Application Priority Data
Sep. 1, 2020 (CN) .......................... 202010906437.7

(51) Int. Cl.
| | |
|---|---|
| *G01N 33/68* | (2006.01) |
| *C07K 14/78* | (2006.01) |
| *G01N 30/72* | (2006.01) |
| *G01N 30/88* | (2006.01) |

(52) U.S. Cl.
CPC ......... *G01N 33/6887* (2013.01); *C07K 14/78* (2013.01); *G01N 30/7233* (2013.01); *G01N 30/88* (2013.01); *G01N 33/6848* (2013.01); *G01N 2030/8831* (2013.01); *G01N 2333/944* (2013.01)

(58) Field of Classification Search
None
See application file for complete search history.

(56) References Cited

U.S. PATENT DOCUMENTS

2007/0031501 A1    2/2007    Van Es et al.

FOREIGN PATENT DOCUMENTS

| CN | 101693737 A | 4/2010 |
|---|---|---|
| CN | 105273061 A | 1/2016 |
| CN | 106841497 A | 6/2017 |
| CN | 109187835 A | 1/2019 |
| CN | 111239302 A | 6/2020 |

OTHER PUBLICATIONS

Liu et al.,"A strategy for identifying species-specific peptide biomarkers in deer-hide gelatin using untargeted and targeted mass spectrometry approaches", Analytica Chimica Acta 1092: 32-41 (Year: 2019).*
Cheng et al.,"Identification of five gelatins by ultra performance liquid chromatography/time-of-flight mass spectrometry (UPLC/Q-TOF-MS) using principal component analysis", Journal of Pharmaceutical and Biomedical Analysis 62: 191-195 (Year: 2012).*
Tao Zhang et al.,Identification Studies on Oxhide Gelatin Collagen Based on Nano LC-MS/MS Method Journal of Nanjing University of Chinese Medicine, vol. 36 (1) :Section 3.3 Publication Date: Jan. 31, 2020.
Rui Liu et al.,Comparative Analysis of Material Basis of Deerskin and Deerskin Glue Based on"Polypeptide group-modification group" Chinese Journal of Pharmaceutical Sciences, vol. 55 (8): Abstract and Section 3 Publication Date: Aug. 12, 2020.

* cited by examiner

*Primary Examiner* — Anand U Desai
(74) *Attorney, Agent, or Firm* — CBM PATENT CONSULTING, LLC

(57) ABSTRACT

Disclosed are a deer-derived specific peptide and a detection method therefor; by screening through a large number of experiments, a ratio of relative contents of two deer-derived peptides is determined, and a graph is drawn by using a proportion of a deer antler gelatin in a mixed gelatin as an abscissa and using a value of $A_{peptide\ 1}/A_{peptide\ 2}$ as an ordinate; the proportion of the deer antler gelatin is linear with $A_{peptide\ 1}/A_{peptide\ 2}$ as a standard curve equation to distinguish a deer hide gelatin from the deer antler gelatin; the method can be used for distinguishing the deer antler gelatin from the deer hide gelatin, and controlling the quality; a defect in the prior art that the deer antler gelatin and the deer hide gelatin are difficult to distinguish in appearance, and are also difficult to distinguish by using a specific peptide fragment, is solved.

5 Claims, 2 Drawing Sheets

Specification includes a Sequence Listing.

SEQUENCE LISTING

<160> NUMBER OF SEQ ID NOS: 2

<210> SEQ ID NO 1
<211> LENGTH: 30
<212> TYPE: PRT

```
<213> ORGANISM: Artificial Sequence
<220> FEATURE:
<223> OTHER INFORMATION: It is synthesized
<220> FEATURE:
<221> NAME/KEY: MOD_RES
<222> LOCATION: (12)..(12)
<223> OTHER INFORMATION: Xaa can be 3-Hydroxyproline or 4-Hydroxyproline
<220> FEATURE:
<221> NAME/KEY: MOD_RES
<222> LOCATION: (21)..(21)
<223> OTHER INFORMATION: Xaa can be 3-Hydroxyproline or 4-Hydroxyproline
<220> FEATURE:
<221> NAME/KEY: MOD_RES
<222> LOCATION: (24)..(24)
<223> OTHER INFORMATION: Xaa can be 3-Hydroxyproline or 4-Hydroxyproline

<400> SEQUENCE: 1

Gly Asn Asp Gly Ala Thr Gly Ala Ala Gly Pro Xaa Gly Pro Thr Gly
1               5                   10                  15

Pro Ala Gly Pro Xaa Gly Phe Xaa Gly Ala Val Gly Ala Lys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: It is synthesized
<220> FEATURE:
<221> NAME/KEY: MOD_RES
<222> LOCATION: (12)..(12)
<223> OTHER INFORMATION: Xaa can be 3-Hydroxyproline or 4-Hydroxyproline
<220> FEATURE:
<221> NAME/KEY: MOD_RES
<222> LOCATION: (21)..(21)
<223> OTHER INFORMATION: Xaa can be 3-Hydroxyproline or 4-Hydroxyproline

<400> SEQUENCE: 2

Gly Asn Asp Gly Ala Thr Gly Ala Ala Gly Pro Xaa Gly Pro Thr Gly
1               5                   10                  15

Pro Ala Gly Pro Xaa Gly Phe Pro Gly Ala Val Gly Ala Lys
            20                  25                  30
```

DEER-DERIVED SPECIFIC PEPTIDE AND DETECTION METHOD THEREFOR

TECHNICAL FIELD

The present invention relates to a deer-derived specific peptide and a detection method therefor, in particular to a specific peptide for distinguishing a deer antler gelatin from a deer hide gelatin, as well as a sample adulterated with the deer hide gelatin in the deer antler gelatin and a proportion of the deer hide gelatin adulterated, and a detection method.

BACKGROUND

Gelatin medicinal materials comprise donkey-hide gelatin, deer hide gelatin, deer hide gelatin, cattle hide gelatin, and the like, and more than 80% of which are collagen of different types, comprising collagen type I alpha 1 chain (COL1A1), collagen type I alpha 2 chain (COL1A2), collagen type II alpha 1 chain (COL2A1), collagen type III alpha 1 chain (COL3A1), and the like, wherein the peptides from the collagen type I alpha 1 (COL1) are prevailing. COL1, as a highly conservative protein, widely exists in different animal species, and is one of the important protein components of the gelatin medicinal material.

Both the deer antler gelatin and the deer hide gelatin are from *Cervus nippon* Temminck or *Cervus elaphus* Linnaeus, which are valuable Chinese medicinal materials. The deer antler gelatin is a gelatin stick made by decocting and concentrating *Cervus nippon* Temminck or *Cervus elaphus* Linnaeus antlers, while the deer hide gelatin is a gelatin stick made by decocting and concentrating dried skin or fresh skin of *Cervus nippon* Temminck or *Cervus elaphus* Linnaeus. The antlers are ossified horns of *Cervus elaphus* Linnaeus or *Cervus nippon* Temminck, and the prices of which are much higher than that of the deer hide. In the market, there is a phenomenon of adulterating the deer hide gelatin into the deer antler gelatin. How to distinguish the deer antler gelatin from the deer hide gelatin is really a difficult problem in the identification research of the gelatin medicinal materials, which brings challenges to the identification of the deer antler gelatin and the deer hide gelatin, as well as the identification of the deer antler gelatin adulterated with the deer hide gelatin.

It is difficult to distinguish the deer antler gelatin from the deer hide gelatin in appearance, and both of the deer antler gelatin and the deer hide gelatin are from *Cervus nippon* Temminck or *Cervus elaphus* Linnaeus, and have the same protein compositions. Therefore, it is basically impossible to distinguish the deer antler gelatin and the deer hide gelatin by searching for species-specific peptides.

SUMMARY

Object of the present invention: the present invention determines a ratio of relative contents of two deer-derived peptides by screening through a large number of experiments, so as to be used for distinguishing a deer antler gelatin from a deer hide gelatin. The method is strong in specificity, high in sensitivity and simple in operation, and can be used for distinguishing the deer antler gelatin from the deer hide gelatin, and controlling the quality.

In order to achieve the above object, the present invention adopts the following technical solutions:

A deer-derived specific peptide, wherein the specific peptide comprises:

peptide 1:
Gly-Asn-Asp-Gly-Ala-Thr-Gly-Ala-Ala-Gly-Pro-Hyp-Gly-Pro-Thr-Gly-Pro-Ala-Gly-Pro-Hyp-Gly-Phe-Hyp-Gly-Ala-Val-Gly-Ala-Lys (SEQ ID NO:01); and peptide 2:
Gly-Asn-Asp-Gly-Ala-Thr-Gly-Ala-Ala-Gly-Pro-Hyp-Gly-Pro-Thr-Gly-Pro-Ala-Gly-Pro-Hyp-Gly-Phe-Pro-Gly-Ala-Val-Gly-Ala-Lys (SEQ ID NO:02).

A detection method for a deer-derived specific peptide, comprises the following steps of:
(1) preparing the above two deer-derived specific peptides into a mixed control solution;
(2) subjecting deer hide gelatin and deer antler gelatin samples to be detected to enzyme digestion with trypsin, then injecting the enzymatic hydrolysate and the mixed control solution of the deer-derived specific peptides in the step (1) into a liquid chromatograph/mass spectrometer, taking the deer-derived specific peptides as control, and adopting an ESI positive ion mode and a multi-reaction monitoring mode for detection, wherein selected ion pairs comprise: peptide 1: M/z 850.4 (triple charge)→515.4, peptide 2: m/z 845.0 (triple charge)→507.3; and determining whether the sample is a deer hide gelatin or a deer antler gelatin by a ratio of a peak area $A_{peptide\ 1}$ of the peptide 1 to a peak area $A_{peptide\ 2}$ of the peptide 2.

As a preferred solution, in the detection method for the deer-derived specific peptide, the enzyme digestion method comprises the following steps of: adding 5 ml of phosphate buffer solution (pH=6.0 to 8.5) into 10 mg of gelatin medicinal material sample to be detected, completely dissolving the sample by ultrasound, centrifuging the solution at 12,000 rpm for 20 minutes, placing 150 μl of supernatant into a 2 ml centrifuge tube, diluting the supernatant with 1 ml of 50 mM PBS, adding a proper amount of trypsin, shaking the mixture evenly for full enzymolysis, adding 60 μl of 10% v/v trifluoroacetic acid (TFA) solution to stop the reaction, centrifuging the solution at 12,000 rpm for 20 minutes to obtain the enzymatic hydrolysate of the gelatin medicinal material, and placing the enzymatic hydrolysate at −20° C. for storage and later use. An amount of the trypsin added ranges from 0.1 wt % to 10 wt %. The enzymolysis method comprises: any one or a combination of more of constant-temperature enzymolysis at 37° C., microwave-assisted enzymolysis under 500 W to 1,000 W, ultrasonic-assisted enzymolysis under 20 kHz to 100 kHz and enzyme-immobilized enzymolysis.

As a preferred solution, in the detection method for the deer-derived specific peptide above, liquid phase conditions for detection by the liquid chromatograph/mass spectrometer are as follows: a chromatographic column is a 1.7 μm Waters C18 column with a specification of 2.1 μm×100 mm, a sample size of 2 μl and a flow rate of 0.3 ml/min; 10% to 30% A linear gradient elution lasts for 0 to 3.5 minutes, 30% to 10% A linear gradient elution lasts for 3.5 minutes to 4 minutes, and 10% A linear gradient elution lasts for 4 minutes to 6 minutes; and a triple quadrupole mass spectrometry is used, and a mass spectrometry condition is: m/z 850.4 (triple charge)→515.4, m/z 845.0 (triple charge) →507.3.

As a preferred solution, in the detection method for the deer-derived specific peptide above, $A_{peptide\ 1}/A_{peptide\ 2}$ of the deer antler gelatin is no lower than 5.5, while $A_{peptide\ 1}/A_{peptide\ 2}$ of the deer hide gelatin is no higher than 1.2. Further, $A_{peptide\ 1}/A_{peptide\ 2}$ of the pure deer antler gelatin is no lower than 5.7, while $A_{peptide\ 1}/A_{peptide\ 2}$ of the pure deer hide gelatin is no higher than 1.2.

A detection kit for a deer antler gelatin and a deer hide gelatin, wherein the kit comprises the two deer-derived specific peptides above. Certainly, other necessary reagents for liquid quality detection may also be comprised according to the need.

According to the method and the kit of the present invention, whether the sample to be detected is pure deer antler gelatin or pure deer hide gelatin can be determined, and the proportion of the deer hide gelatin to the deer antler gelatin in the mixed gelatin can also be determined.

A method for detecting a proportion of a deer hide gelatin to a deer antler gelatin provided by the present invention comprises the following steps of:

(1) preparing the two deer-derived specific peptides according to claim 1 into a mixed control solution; (2) mixing the deer antler gelatin and the deer hide gelatin according to proportions of 0%, 10%, 20%, 30%, 40%, 50%, 60%, 70%, 80%, 90% and 100% respectively, adding 5 ml of phosphate buffer solution (pH=6.0 to 8.5) into 10 mg of mixed gelatin sample in each batch, completely dissolving the sample by ultrasound, centrifuging the solution at 12,000 rpm for 20 minutes, placing 150 µl of supernatant into a 2 ml centrifuge tube, diluting the supernatant with 1 ml of 50 mM PBS, adding trypsin with a mass concentration of 1%, shaking the mixture evenly for microwave enzymolysis for 30 minutes, adding 60 µl of 10% trifluoroacetic acid solution to stop the reaction after enzymolysis, centrifuging the solution at 12,000 rpm for 20 minutes to obtain enzymolysis solutions of mixed gelatin samples with different proportions, and placing the enzymolysis solutions at −20° C. for storage and later use; and (2) injecting the enzymatic hydrolysates of the mixed gelatin samples with different proportions obtained in the step (2) and the mixed control solution of the deer-derived specific peptides obtained in the step (1) into the liquid chromatograph/mass spectrometer, taking the deer-derived specific peptides as control, and adopting an ESI positive ion mode and a multi-reaction monitoring mode for detection, wherein a sample size is 1 µg, and liquid phase conditions for detection by the liquid chromatograph/mass spectrometer are as follows: a chromatographic column is a 1.7 µm C18 reversed phase column with a specification of 2.1 µm×100 mm and a flow rate of 0.3 ml/min, a mobile phase A is acetonitrile, a mobile phase B is 0.1% formic acid, 10% to 30% A linear gradient elution lasts for 0 to 3.5 minutes, 30% to 10% A linear gradient elution lasts for 3.5 minutes to 4 minutes, and 10% A elution lasts for 4 minutes to 6 minutes; and a mass spectrometry condition for detection by the liquid chromatograph/mass spectrometer is: an electrospray positive ion mode ESI+, and mass spectrometry parameters comprise: an ion source temperature of 500° C.; an ionization voltage of 5,500 V; a desolvent temperature of 500° C.; an ion source gas 1 of 60 psi; and an ion source gas 2 of 60 psi;

setting the ion pair conditions corresponding to the specific peptides as follows:

peptide 1: M/z 850.4 (triple charge)→515.4, DP=162.49, CE=32.87; and peptide 2: m/z 845.0 (triple charge)→507.3, DP=162.52, CE=31.51; and drawing a graph by using a proportion of the deer antler gelatin in the mixed gelatin as an abscissa and using a value of $A_{peptide\ 1}/A_{peptide\ 2}$ as an ordinate, and since the proportion of the deer antler gelatin has a linear relationship to $A_{peptide\ 1}/A_{peptide\ 2}$, establishing a standard curve equation as: y=4.7903x+0.4106, and $R^2$=0.9669; and since the proportion of the deer antler gelatin adulterated has a linear relationship with peak values of the peptide 1 and the peptide 2, calculating a proportion of $A_{peptide\ 1}/A_{peptide\ 2}$ according to the standard curve equation, and determining a mixing proportion of the deer antler gelatin and the deer hide gelatin.

Beneficial effects: compared with the prior art, the present invention has the following advantages.

The present invention determines the ratio of the relative contents of the two deer-derived peptides by screening through a large number of experiments, so as to be used for distinguishing the deer antler gelatin from the deer hide gelatin. The method is strong in specificity, high in sensitivity and simple in operation, and can be used for distinguishing the deer antler gelatin from the deer hide gelatin, and controlling the quality. The present invention can overcome the shortcomings of the prior art, such as the difficulty in distinguishing the deer antler gelatin from the deer hide gelatin in appearance and the difficulty in distinguishing specific peptides, and has made very good technical progress.

DETAILED DESCRIPTION

The present invention will be further described in detail hereinafter with reference to the specific embodiments, but the present invention is not limited to these embodiments.

The trypsin used in the following embodiments was purchased from Promega Company.

Embodiment 1

A deer-derived specific peptide had two specific peptide sequences, as shown in sequence table 1:

peptide 1:
Gly-Asn-Asp-Gly-Ala-Thr-Gly-Ala-Ala-Gly-Pro-Hyp-Gly-Pro-Thr-Gly-Pro-Ala-Gly-Pro-Hyp-Gly-Phe-Hyp-Gly-Ala-Val-Gly-Ala-Lys; and peptide 2:
Gly-Asn-Asp-Gly-Ala-Thr-Gly-Ala-Ala-Gly-Pro-Hyp-Gly-Pro-Thr-Gly-Pro-Ala-Gly-Pro-Hyp-Gly-Phe-Pro-Gly-Ala-Val-Gly-Ala-Lys.

The polypeptides above were prepared by Nanjing GenScript Biotech Corporation using a solid phase synthesis method.

Embodiment 2 Proportional relationship between peptide 1 and peptide 2 of deer hide gelatin batches of commercially available deer hide gelatin samples were taken, with each batch of about 10 mg, added with 5 ml of phosphate buffer solution (pH=7.8), the samples were completely dissolved by ultrasound, centrifuged at 12,000 rpm for 20 minutes, 150 µl of supernatant were placed into a 2 ml centrifuge tube, diluted with 1 ml of 50 mM PBS, added with 1 wt % trypsin, shaken evenly, and enzymolyzed at a constant temperature of 37° C. for 12 hours. After enzymolysis, 60 µl of 10% v/v TFA solution was added to stop the reaction, and then centrifuged at 12,000 rpm for 20 minutes to obtain the enzymatic hydrolysate of the deer hide gelatin medical material, which was stored at −20° C. for later use.

Figure 2:
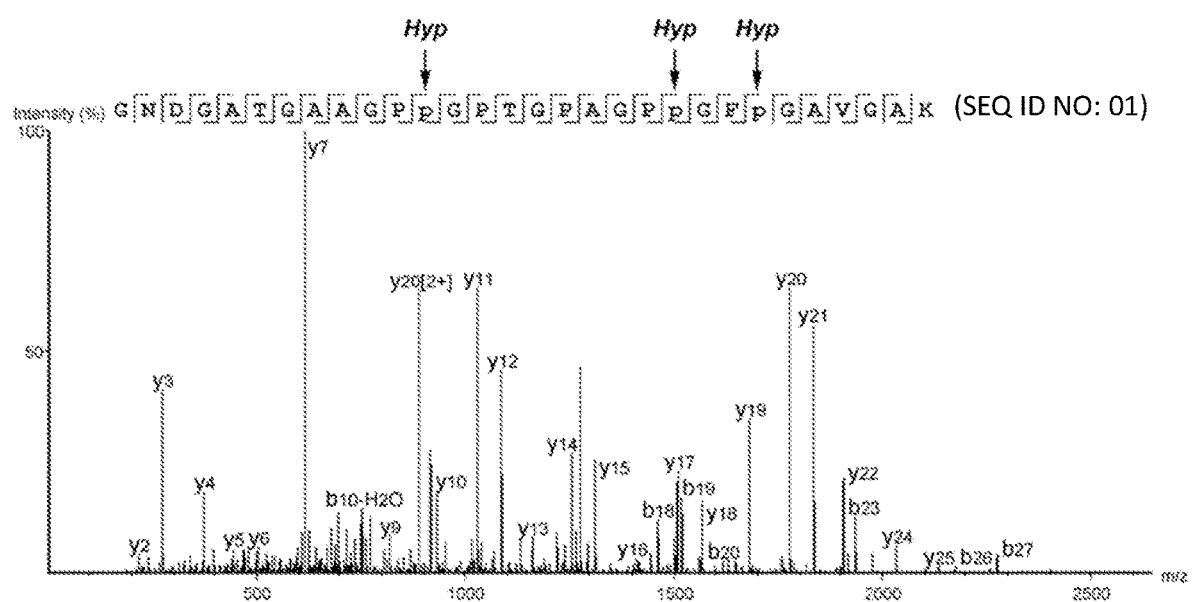
FIG. 2 is a mass spectrogram of the peptide 1.
Figure 3:
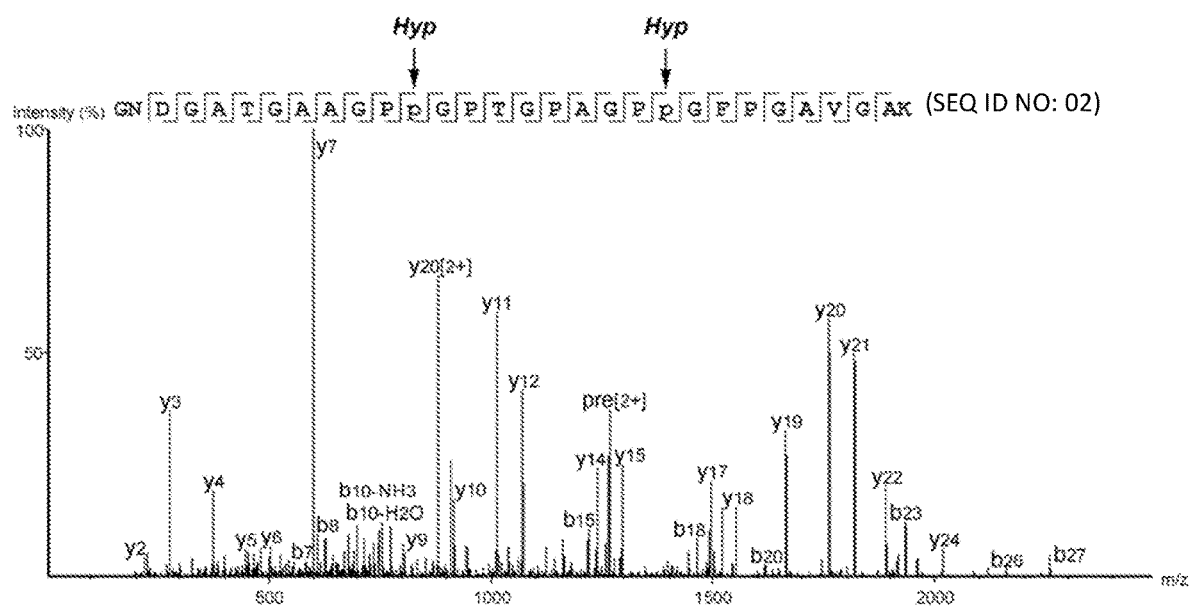
FIG. 3 is a mass spectrogram of the peptide 2.

The enzymatic hydrolysates of each batch of deer hide gelatin were injected into the liquid chromatograph/mass spectrometer for detection, wherein a sample size was 1 μg, and liquid phase conditions for detection by the liquid chromatograph/mass spectrometer were as follows: a chromatographic column was a 1.7 μm C18 reversed phase column (2.1 μm×100 mm) with a flow rate of 0.3 ml/min, a mobile phase A was acetonitrile, a mobile phase B was 0.1% formic acid, 10% to 30% A linear gradient elution lasted for 0 to 3.5 minutes, 30% to 10% A linear gradient elution lasts for 3.5 minutes to 4 minutes, and 10% A elution lasts for 4 minutes to 6 minutes. A mass spectrometry condition for detection by the liquid chromatograph/mass spectrometer was: an electrospray positive ion mode ESI+, and mass spectrometry parameters comprised: an ion source temperature of 500° C.; an ionization voltage of 5,500 V; a desolvent temperature of 500° C.; an ion source gas 1 of 60 psi; and an ion source gas 2 of 60 psi. The mass spectra were shown in FIG. 2 and FIG. 3. The ion pair conditions corresponding to the specific peptides were set as follows:

peptide 1: M/z 850.4 (triple charge)→515.4, DP=162.49, CE=32.87; and peptide 2: m/z 845.0 (triple charge)→507.3, DP=162.52, CE=31.51.

The values of $A_{peptide\ 1}/A_{peptide\ 2}$ in the 10 batches of deer hide gelatin were shown in Table 1. The average value of $A_{peptide\ 1}/A_{peptide\ 2}$ was 0.0.612±0.282.

TABLE 1

Results of $A_{peptide\ 1}/A_{peptide\ 2}$ in deer hide gelatin

| Batch | $A_{peptide\ 1}$ | $A_{peptide\ 2}$ | $A_{peptide\ 1}/A_{peptide\ 2}$ | Average value of $A_{peptide\ 1}/A_{peptide\ 2}$ |
|---|---|---|---|---|
| Deer hide gelatin-1 | 117972 | 285071 | 0.414 | 0.612 ± 0.282 |
| Deer hide gelatin-2 | 94534 | 197073 | 0.480 | |
| Deer hide gelatin-3 | 147007 | 335823 | 0.438 | |
| Deer hide gelatin-4 | 93660 | 88906 | 1.053 | |
| Deer hide gelatin-5 | 124893 | 146508 | 0.852 | |
| Deer hide gelatin-6 | 103489 | 282973 | 0.366 | |
| Deer hide gelatin-7 | 128678 | 115750 | 1.112 | |
| Deer hide gelatin-8 | 73454 | 181928 | 0.404 | |
| Deer hide gelatin-9 | 77833 | 155640 | 0.500 | |
| Deer hide gelatin-10 | 99419 | 197361 | 0.504 | |

Embodiment 3 Proportional relationship between peptide 1 and peptide 2 of deer antler gelatin batches of deer antler samples were taken and prepared into deer antler gelatin samples according to the method of preparing deer antler gelatin in Chinese Pharmacopoeia 2020, with each batch of 10 mg, added with 5 ml of phosphate buffer solution (pH=7.8), the samples were completely dissolved by ultrasound, centrifuged at 12,000 rpm for 20 minutes, 150 μl of supernatant were placed into a 2 ml centrifuge tube, diluted with 1 ml of 50 mM PBS, added with 1 wt % trypsin, shaken evenly, and enzymolyzed by ultrasound for 10 minutes. After enzymolysis, 60 μl of 10% v/v TFA solution was added to stop the reaction, and then centrifuged at 12,000 rpm for 20 minutes to obtain the enzymatic hydrolysate of the deer antler gelatin, which was stored at −20° C. for later use.

The enzymatic hydrolysates of each batch of deer antler gelatin were injected into the liquid chromatograph/mass spectrometer for detection, wherein a sample size was 1 μg, and liquid phase conditions for detection by the liquid chromatograph/mass spectrometer were as follows: a chromatographic column was a 1.7 μm C18 reversed phase column (2.1 μm×100 mm) with a flow rate of 0.3 ml/min, a mobile phase A was acetonitrile, a mobile phase B was 0.1% formic acid, 10% to 30% A linear gradient elution lasted for 0 to 3.5 minutes, 30% to 10% A linear gradient elution lasted for 3.5 minutes to 4 minutes, and 10% A elution lasted for 4 minutes to 6 minutes. A mass spectrometry condition for detection by the liquid chromatograph/mass spectrometer was: an electrospray positive ion mode ESI+, and mass spectrometry parameters comprised: an ion source temperature of 500° C.; an ionization voltage of 5,500 V; a desolvent temperature of 500° C.; an ion source gas 1 of 60 psi; and an ion source gas 2 of 60 psi. The mass spectra were shown in FIG. 2 and FIG. 3. The ion pair conditions corresponding to the specific peptides were set as follows:

peptide 1: M/z 850.4 (triple charge)→515.4, DP=162.49, CE=32.87; and peptide 2: m/z 845.0 (triple charge)→507.3, DP=162.52, CE=31.51.

The values of $A_{peptide\ 1}/A_{peptide\ 2}$ in the 10 batches of deer antler gelatin were shown in Table 2. The average value of $A_{peptide\ 1}/A_{peptide\ 2}$ was 7.428±1.617.

TABLE 2

Results of $A_{peptide\ 1}/A_{peptide\ 2}$ in deer antler gelatin

| Batch | $A_{peptide\ 1}$ | $A_{peptide\ 2}$ | $A_{peptide\ 1}/A_{peptide\ 2}$ | Average value of $A_{peptide\ 1}/A_{peptide\ 2}$ |
|---|---|---|---|---|
| Deer antler gelatin-1 | 1733347 | 238417 | 7.270 | 7.428 ± 1.617 |
| Deer antler gelatin-2 | 1874077 | 205064 | 9.139 | |
| Deer antler gelatin-3 | 1736568 | 289973 | 5.989 | |
| Deer antler gelatin-4 | 1217432 | 182921 | 6.656 | |
| Deer antler gelatin-5 | 1739091 | 289409 | 6.009 | |
| Deer antler gelatin-6 | 1859076 | 246296 | 7.548 | |
| Deer antler gelatin-7 | 1802154 | 186993 | 9.638 | |
| Deer antler gelatin-8 | 1945171 | 311810 | 6.238 | |
| Deer antler gelatin-9 | 1758124 | 175207 | 10.035 | |
| Deer antler gelatin-10 | 1418918 | 246354 | 5.760 | |

Embodiment 4 Proportional relationships between peptide 1 and peptide 2 in mixed samples of deer hide gelatin and deer antler gelatin with different proportions The deer antler gelatin and the deer hide gelatin were mixed according to proportions of 0%, 10%, 20%, 30%, 40%, 50%, 60%, 70%, 80%, 90% and 100%, respectively added with 5 ml of phosphate buffer solution (pH-7.8) into about 10 mg of mixed gelatin sample in each batch, the sample was completely dissolved by ultrasound, centrifuged at 12,000 rpm for 20 minutes, 150 μl of supernatant was placed into a 2 ml centrifuge tube, diluted with 1 ml of 50 mM PBS, added with 1 wt % trypsin, shaken evenly for microwave enzymolysis for 30 minutes, added with 60 μl of 10% v/v TFA solution to stop the reaction after enzymolysis, centrifuged at 12,000 rpm for 20 minutes to obtain enzymolysis solutions of mixed gelatin samples with different proportions, which were stored at −20° C. for later use.

The enzymatic hydrolysates of the mixed gelatin samples with different proportions were injected into the liquid chromatograph/mass spectrometer, wherein a sample size was 1 μg, and liquid phase conditions for detection by the liquid chromatograph/mass spectrometer are as follows: a chromatographic column was a 1.7 μm C18 reversed phase column (2.1 μm×100 mm) with a flow rate of 0.3 ml/min, a mobile phase A was acetonitrile, a mobile phase B was 0.1% formic acid, 10% to 30% A linear gradient elution lasted for 0 to 3.5 minutes, 30% to 10% A linear gradient elution lasted for 3.5 minutes to 4 minutes, and 10% A elution lasted for 4 minutes to 6 minutes. A mass spectrometry condition for detection by the liquid chromatograph/mass spectrometer was: an electrospray positive ion mode ESI+, and mass spectrometry parameters comprised: an ion source temperature of 500° C.; an ionization voltage of 5,500 V; a desolvent temperature of 500° C.; an ion source gas 1 of 60 psi; and an ion source gas 2 of 60 psi. The mass spectra were shown in FIG. 2 and FIG. 3. The ion pair conditions corresponding to the specific peptides were set as follows:

peptide 1: M/z 850.4 (triple charge)→515.4, DP=162.49, CE=32.87; and peptide 2: m/z 845.0 (triple charge)→507.3, DP=162.52, CE=31.51.

Figure 1:
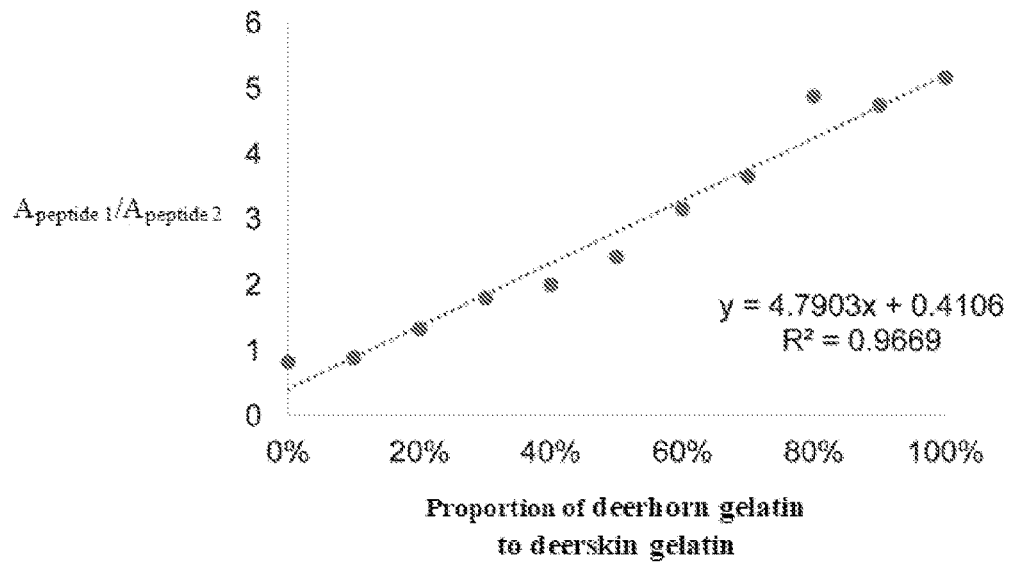
FIG. 1 shows a numerical relationship between a proportion of a deer antler gelatin in a mixed gelatin and $A_{peptide\ 1}/A_{peptide\ 2}$.

Values of $A_{peptide\ 1}/A_{peptide\ 2}$ of mixed gelatin samples with different proportions were shown in Table 3, and a numerical relationship between the proportion of the deer antler gelatin in the mixed gelatin and $A_{peptide\ 1}/A_{peptide\ 2}$ was shown in FIG. 1. A graph was drawn by using the proportion of the deer antler gelatin in the mixed gelatin as an abscissa and using the value of $A_{peptide\ 1}/A_{peptide\ 2}$ as an ordinate, and the proportion of the deer antler gelatin had a linear relationship to $A_{peptide\ 1}/A_{peptide\ 2}$, y=4.7903x+0.4106, and $R^2$=0.9669. It was indicated that the proportion of the deer antler gelatin adulterated was related to the peak areas of the peptide 1 and the peptide 2. Therefore, the mixing proportion of the deer antler gelatin and the deer hide gelatin could be determined according to the ratio of $A_{peptide\ 1}/A_{peptide\ 2}$.

TABLE 3

Relationship between the mixing proportion of the deer antler gelatin/deer hide gelatin mixed sample and the peak area

| Mixed gelatin proportion | | Peak area | | Peak area ratio |
|---|---|---|---|---|
| Proportion of deer antler gelatin % | Proportion of deer hide gelatin % | Peptide 1 | Peptide 2 | $A_{peptide\ 1}/A_{peptide\ 2}$ |
| 0 | 100 | 341004 | 415023 | 0.822 |
| 10 | 90 | 329057 | 370689 | 0.888 |
| 20 | 80 | 513434 | 387355 | 1.325 |
| 30 | 70 | 755737 | 419440 | 1.802 |
| 40 | 60 | 770995 | 385569 | 2.000 |
| 50 | 50 | 1076657 | 443720 | 2.426 |
| 60 | 40 | 1140066 | 361642 | 3.152 |
| 70 | 30 | 1449246 | 396946 | 3.651 |
| 80 | 20 | 1755511 | 359593 | 4.882 |
| 90 | 10 | 1710217 | 360363 | 4.746 |
| 100 | 0 | 2179560 | 421602 | 5.170 |

Embodiment 5

Mixed control of the peptide 1 and the peptide 2 with a certain concentration were taken, and fed for six times continuously under the above-mentioned chromatography-mass spectrometry conditions, to determine the peak areas of the control of the peptide 1 and the peptide 2, and calculate the RSD of the peak areas of the control. The results were shown in Table 4, and the RSD of the peptide 1 and the peptide 2 were respectively 1.10% and 1.67%, indicating that the method had excellent precision.

A corresponding concentration when a signal-to-noise ratio (S/N) of the peptide 1 and the peptide 2 was about 3, was taken as a limit of detection (LOD), and a corresponding concentration when the signal-to-noise ratio (S/N) of the peptide 1 and the peptide 2 was about 10, was taken as a limit of quantitation (LOQ). The results were shown in Table 4, and the LOQ and the LOD of the peptide 1 were 0.72 ng/ml and 0.24 ng/ml respectively. The LOQ and the LOD of the peptide 2 were 2.40 ng/ml and 0.80 ng/ml respectively.

TABLE 4

Precision, limit of detection and limit of quantitation of peptide 1 and peptide 2

| | Precision (RSD, %) | LOQ (ng/ml) | LOD (ng/ml) |
|---|---|---|---|
| Peptide 1 | 1.10 | 0.72 | 0.24 |
| Peptide 2 | 1.67 | 2.40 | 0.80 |

What is claimed is:

1. A detection method for a specific peptide capable of distinguishing a deer antler gelatin from a deer hide gelatin, comprising the following steps of:
   (i) preparing two deer-derived characteristic peptides, peptide 1 and peptide 2, dissolving the peptide 1 and the peptide 2 in water to yield a mixed control solution; and
   (ii) digesting a deer gelatin sample from *Cervus nippon* Temminck or *Cervus elaphus* Linnaeus with trypsin to yield an enzymatic hydrolysate, then injecting the enzymatic hydrolysate and the mixed control solution into a liquid chromatograph/mass spectrometer, taking the peptide 1 and the peptide 2 as controls, and adopting an ESI positive ion mode and a multi-reaction monitoring mode for detection, wherein selected ion pairs comprise: the peptide 1: m/z 850.4 triple charge→515.4, the peptide 2: m/z 845.0 triple charge→507.3; and determining whether the deer gelatin sample is the deer hide gelatin derived from *Cervus elaphus* Linnaeus or the deer antler gelatin derived from *Cervus nippon* Temminck by a ratio of a peak area $A_{peptide\ 1}$ of the peptide 1 to a peak area $A_{peptide\ 2}$ of the peptide 2; $A_{peptide\ 1}/A_{peptide\ 2}$ of the deer antler gelatin is higher than 5.5, while $A_{peptide\ 1}/A_{peptide\ 2}$ of the deer hide gelatin is lower than 1.2;
   wherein
   the peptide 1 has the amino acid sequence shown as SEQ ID NO: 01;
   and
   the peptide 2 has the amino acid sequence shown as SEQ ID NO: 02;
   liquid phase conditions for detection by the liquid chromatograph/mass spectrometer are as follows: a chromatographic column is a 1.7 μm HPLC column with a specification of 2.1 μm×100 mm, a sample size of 2 μl and a flow rate of 0.3 ml/min; 10% to 30% A linear gradient elution lasts for 0 to 3.5 minutes, 30% to 10% A linear gradient elution lasts for 3.5 minutes to 4 minutes, and 10% A linear gradient elution lasts for 4 minutes to 6 minutes.

2. The detection method according to claim 1, wherein a method for the digesting the deer gelatin sample comprises: adding 5 ml of phosphate buffer solution into 10 mg of the deer gelatin sample, completely dissolving the sample by ultrasound to yield a solution, then centrifuging the solution at 12,000 rpm for 20 minutes, taking and transferring 150 μl of supernatant from the centrifuged solution into a 2 ml centrifuge tube, diluting the supernatant with 1 ml of 50 mM PBS, adding the trypsin to yield a mixture, shaking the mixture evenly for an enzymolysis, adding 60 µl of 10% v/v trifluoroacetic acid solution to stop the mixture, centrifuging the mixture at 12,000 rpm for 20 minutes to obtain the enzymatic hydrolysate.

3. The detection method according to claim 2, wherein an amount of the trypsin is from 0.1 wt % to 10 wt %.

4. The detection method according to claim 2, wherein the enzymolysis is selected from the group consisting of constant-temperature enzymolysis at 37° C., microwave-assisted enzymolysis, ultrasonic-assisted enzymolysis and enzyme-immobilized enzymolysis.

5. A detection method for a specific peptide capable of distinguishing a deer antler gelatin from a deer hide gelatin, comprising the following steps of:

(i) Establishment of Linear Relationship mixing the deer antler gelatin and the deer hide gelatin according to proportions of 0%, 10%, 20%, 30%, 40%, 50%, 60%, 70%, 80%, 90% and 100% respectively, adding 5 ml of phosphate buffer solution into 10 mg of mixed gelatin sample in each batch, completely dissolving the sample by ultrasound to yield a solution, centrifuging the solution at 12,000 rpm for 20 minutes, taking and transferring 150 µl of supernatant from the centrifuged solution into a 2 ml centrifuge tube, diluting the supernatant with 1 ml of 50 mM PBS, adding trypsin with a mass concentration of 1% to yield a mixture, shaking the mixture evenly for microwave enzymolysis for 30 minutes, adding 60 µl of 10% trifluoroacetic acid solution to stop the enzymolysis to yield an enzymolysis solution, centrifuging the enzymolysis solution at 12,000 rpm for 20 minutes to obtain enzymatic solutions of mixed gelatin samples with different proportions; and injecting the enzymatic hydrolysates of the mixed gelatin samples with different proportions into a liquid chromatograph/mass spectrometer, a sample size is 1 µg, and liquid phase conditions for detection by the liquid chromatograph/mass spectrometer are as follows: a chromatographic column is a 1.7 µm $C_{18}$ reversed phase column with a specification of 2.1 µm×100 mm and a flow rate of 0.3 ml/min, a mobile phase A is acetonitrile, a mobile phase B is 0.1% formic acid, 10% to 30% A linear gradient elution lasts for 0 to 3.5 minutes, 30% to 10% A linear gradient elution lasts for 3.5 minutes to 4 minutes, and 10% A elution lasts for 4 minutes to 6 minutes; and a mass spectrometry condition for detection by the liquid chromatograph/mass spectrometer is: an electrospray positive ion mode ESI+, and mass spectrometry parameters comprise: an ion source temperature of 500° C.; an ionization voltage of 5,500 V; a desolvent temperature of 500° C.; an ion source gas 1 of 60 psi; and an ion source gas 2 of 60 psi;

setting the ion pair conditions corresponding to specific peptides as follows:

peptide 1: M/z 850.4 triple charge→515.4, DP=162.49, CE=32.87; and peptide 2: m/z 845.0 triple charge→507.3, DP=162.52, CE=31.51; and drawing a graph by using a proportion of the deer antler gelatin in the mixed gelatin as an abscissa and using a value of $A_{peptide\ 1}/A_{peptide\ 2}$ as an ordinate, and since the proportion of the deer antler gelatin has a linear relationship to $A_{peptide\ 1}/A_{peptide}$ 2, establishing a standard curve equation as: y=4.7903x+0.4106, and $R^2$=0.9669; and since the proportion of the deer antler gelatin adulterated has a linear relationship with peak values of the peptide 1 and the peptide 2, calculating a ratio of $A_{peptide\ 1}/A_{peptide\ 2}$ according to the standard curve equation, and determining a mixing proportion of the deer antler gelatin and the deer hide gelatin; $A_{peptide\ 1}/A_{peptide\ 2}$ of the deer antler gelatin is equal to or higher than 5.5, while $A_{peptide\ 1}/A_{peptide\ 2}$ of the deer hide gelatin is equal to or lower than 1.2;

the peptide 1 has the amino acid sequence shown as SEQ ID NO: 1; and the peptide 2 has the amino acid sequence shown as SEQ ID NO: 2.

* * * * *